US011473047B2

(12) United States Patent
Grant (10) Patent No.: US 11,473,047 B2
(45) Date of Patent: Oct. 18, 2022

(54) LIQUID FILTRATION AND PUMP SYSTEM (71) Applicant: The Automation Partnership (Cambridge) Limited, Royston (GB)

(72) Inventor: Paul Grant, Suffolk (GB)

(73) Assignee: The Automation Partnership (Cambridge) Limited, Royston (GB)

( * ) Notice: Subject to any disclaimer, the term of this patent is extended or adjusted under 35 U.S.C. 154(b) by 242 days.

(21) Appl. No.: 16/311,522

(22) PCT Filed: Jul. 18, 2017

(86) PCT No.: PCT/EP2017/068166
§ 371 (c)(1),
(2) Date: Dec. 19, 2018

(87) PCT Pub. No.: WO2018/015406
PCT Pub. Date: Jan. 25, 2018

(65) Prior Publication Data
US 2019/0185803 A1 Jun. 20, 2019

(30) Foreign Application Priority Data
Jul. 19, 2016 (EP) ..................................... 16180187

(51) Int. Cl.
*C12M 1/00* (2006.01)
*C12M 1/12* (2006.01)
(Continued)

(52) U.S. Cl.
CPC ............. *C12M 29/10* (2013.01); *B01D 29/01* (2013.01); *B01D 29/52* (2013.01); *B01D 29/90* (2013.01);
(Continued)

(58) Field of Classification Search
CPC ........ B01D 29/01; B01D 29/52; B01D 29/90; C12M 29/00; C12M 29/04; C12M 29/10;
(Continued)

(56) References Cited

U.S. PATENT DOCUMENTS 4,738,782 A * 4/1988 Yamauchi .......... B01D 67/0093
210/321.84
4,918,019 A * 4/1990 Guinn .................... C12M 29/12
435/286.5
(Continued)

FOREIGN PATENT DOCUMENTS

CN 101835886 A 9/2010
CN 104640973 A 5/2015
(Continued)

OTHER PUBLICATIONS

Web article entitled "Syringe" published by Made How, http://www.madehow.com/Volyme-3/Syringe.html, cached by the Internet Archive on Jul. 9, 2016, accessed Feb. 17, 2022. (Year: 2016).*
(Continued)

*Primary Examiner* — Holly Kipouros
(74) *Attorney, Agent, or Firm* — Klarquist Sparkman, LLP (57) ABSTRACT

A liquid filtration system comprising a syringe pump comprising a gas chamber and a movable plunger, wherein the gas chamber has an aperture at a first end and the plunger forms a seal within the internal walls of the chamber; a liquid chamber having two openings, the openings positioned at opposite ends of the chamber and the first opening connected to the aperture of the gas chamber; a bioreactor in fluidic communication with the second opening of the liquid chamber; a filter arranged to filter liquid passing between the bioreactor and the liquid chamber, the filter comprising a permeate outlet for removing filtered liquid; wherein, in use, the plunger may be moved in a reciprocating motion causing
(Continued)

a corresponding movement of gas which drives liquid alternately between the liquid chamber and the bioreactor such that liquid passes through the filter and filtered liquid may be removed via the permeate outlet.

21 Claims, 4 Drawing Sheets (51) Int. Cl.
    *C12M 1/36*     (2006.01)
    *C12M 1/26*     (2006.01)
    *B01D 29/01*     (2006.01)
    *B01D 29/52*     (2006.01)
    *B01D 29/90*     (2006.01)

(52) U.S. Cl.
    CPC ............ *C12M 29/00* (2013.01); *C12M 29/04* (2013.01); *C12M 29/12* (2013.01); *C12M 33/04* (2013.01); *C12M 37/02* (2013.01); *C12M 37/04* (2013.01); *C12M 41/48* (2013.01); *C12M 47/10* (2013.01)

(58) Field of Classification Search
    CPC ...... C12M 29/12; C12M 33/04; C12M 37/02; C12M 37/04; C12M 41/48; C12M 47/10
    See application file for complete search history.

(56) References Cited

U.S. PATENT DOCUMENTS

| | | | | |
|---|---|---|---|---|
| 6,008,010 | A * | 12/1999 | Greenberger | C12M 41/36 435/813 |
| 2003/0093034 | A1 * | 5/2003 | Chang | A61B 10/025 604/190 |
| 2006/0166351 | A1 * | 7/2006 | Harada | C12N 15/90 435/287.1 |
| 2008/0223463 | A1 * | 9/2008 | Zantl | F16K 99/0001 137/597 |
| 2013/0017131 | A1 * | 1/2013 | Galliher | B01L 1/025 422/243 |
| 2013/0270165 | A1 * | 10/2013 | Shevitz | C12M 29/04 210/205 |
| 2016/0123848 | A1 * | 5/2016 | Griffin | G01N 1/14 435/308.1 |
| 2016/0145563 | A1 * | 5/2016 | Berteau | C12M 41/48 137/15.01 |
| 2016/0349220 | A1 * | 12/2016 | Laustsen | C12M 33/00 |
| 2017/0029871 | A1 * | 2/2017 | Ying | B01L 3/5027 |
| 2018/0298324 | A1 * | 10/2018 | Takeda | C12M 23/12 |

FOREIGN PATENT DOCUMENTS

| | | | | |
|---|---|---|---|---|
| EP | 2863221 | | 4/2015 | |
| WO | WO2012/026978 | | 3/2012 | |
| WO | WO-2012026978 A2 * | | 3/2012 | ............ C12M 29/00 |
| WO | WO2014/051503 | | 4/2014 | |
| WO | WO 2014/051503 A1 | | 4/2014 | |
| WO | WO-2014051503 A1 * | | 4/2014 | ............ C12M 41/40 |
| WO | WO2015/039115 | | 3/2015 | |

OTHER PUBLICATIONS

International Search Report for PCT/EP2017/068166, dated Sep. 19, 2017.
First Office Action for Chinese Publication No. CN201780040570.5, dated May 6, 2021, with English translation (20 pages).

* cited by examiner

LIQUID FILTRATION AND PUMP SYSTEM

CROSS REFERENCE TO RELATED APPLICATIONS

This is the U.S. National Stage of International Application No. PCT/EP2017/068166, filed Jul. 18, 2017, which was published in English under PCT Article 21(2), which in turn claims the benefit of European Patent Application No. 16180187.3, filed Jul. 19, 2016, which is incorporated herein in its entirety.

FIELD OF THE INVENTION

The present invention relates to a liquid filtration system for filtering a liquid such as a cell culture held within a bioreactor.

BACKGROUND OF THE INVENTION

Systems for filtering liquids are well known in the art where they take many different forms with the typical function of separating, concentrating or removing constituent elements of a liquid, mixture or suspension. Such systems are employed in the biotechnology and pharmaceutical industries to extract certain biological products such as proteins produced using cell cultures within a bioreactor.

In traditional fed-batch bioreactor systems, cells are cultured in batches whereby cells are inoculated into a fresh medium and the cells rapidly enter a growth phase during which they consume the medium nutrients and waste products accumulate in the culture in addition to the secreted protein of interest. After a certain period of time, the cells transition into a stationary phase followed by a decay phase as the cell culture is depleted. At the end of the run the protein is separated from the cell culture as a batch. An issue with such systems, particularly in the case of animal cell cultures which typically have lower production rates, is the limited yields of the biological product of interest which may be achieved.

Perfusion bioreactors are a known alternative system in which the cells are kept in culture whilst replenishing the culture media, thereby allowing the maintenance of a high cell concentration over a longer period of time, providing a greater yield of the desired biological product. In order to maintain stable cell culture conditions, filtration is required for clarification, selective removal and concentration of certain constituents of the cell media such that the cell culture may be replenished with fresh media and spent media may be removed.

Typical filtration systems employed in perfusion bioreactors utilise a pump which moves cell culture liquid from a bioreactor through a filter wherein the filtrate, including waste or target products, is removed from the system and the retentate, including live cells, is returned to the bioreactor. Culture media nutrients may then be replenished by a separate system to maintain the cell culture in a steady, equilibrium state. Such prior art devices often employ tangential flow filtration, wherein the majority of the feed flow travels tangentially across the surface of the filter. This system provides a gentle filtration method which does not subject the delicate animal cells to significant forces which might damage the cells. Furthermore the tangential flow of liquid across the filter ensures that deposits in the filter, which might cause a blockage, are washed away during the filtration process, increasing the length of time over which the filtration system may be continually run. Such systems may be arranged such that flow of the liquid is in one direction around a loop, circulating from the bioreactor through the filter and returning to the bioreactor (which will be referred to under the general term "tangential flow filtration" or TFF). Alternatively an arrangement may be used in which only a single connection between the bioreactor and filter is used with the direction of flow alternating such that liquid travel from the bioreactor to the filter and returns to the bioreactor along the same line (referred to as "alternating tangential flow filtration" or ATF).

A range of pumps are used in prior art systems to execute cell perfusion. Typically ATF based processes use a diaphragm pump whilst TFF process may use a peristaltic pump, a multi-chamber diaphragm type pump or a pump with an impeller, driven magnetically where a single use cell contact part is required. There are however a number of issues with such prior art perfusion pumps.

It is becoming increasingly common to utilise single-use bioreactors, avoiding the need to clean reactors and sensors between runs and thus providing a higher throughput. However, the above listed prior art pumps generally employ moving parts which are in contact with the cell culture to provide the necessary forces to move the liquid around the system. The pumps therefore need to be thoroughly cleaned between runs to ensure that there is no contamination of the system which might result in a run having to be aborted. Similarly any failure or breakage of the moving parts, for example due to wear, would result in the contamination of both the pump and cell culture, resulting in considerable down time while the components are cleaned.

Furthermore, high throughput systems for process development often utilise smaller bioreactors which place limits on the size of the pump used in such a physically constrained environment. Accordingly, many of the above prior art pumps are unsuitable due to being too large and it not being possible scale them to an appropriate size or not being compatible with the relatively low flow rates required in such small systems.

Relatedly, if the pump is incorporated into a single use system, a simple, low cost pump is required which may be disposed of (or certain components thereof disposed of) with the other components of the system. Current known pumps are too complex or costly to incorporate or adapt for application in a single use system. A further issue is that no single prior art pump may be applied in both a TFF and ATF system without significant configuration changes.

Finally, prior art pumps such as peristaltic, diaphragm or impeller pumps place significant mechanical stresses on cells within the cell culture which can potentially damage the cells.

There accordingly exists a need for a perfusion system incorporating a perfusion pump which has a simple, low cost configuration such that it may be employed in a single use system. It is further desirable that the pump is able to be scaled to a small enough size such that it may operate within the physical constraints of a small, process development bioreactor. There also exists a need to provide a system in which contact between the moving parts of the pump and the cell culture is minimised and furthermore, a system which may be operated in both TFF and ATF configurations with little adaption of the pump arrangement.

SUMMARY OF THE INVENTION

The present invention seeks to provide a filtration system which incorporates a low cost pump with a simple design such that it may be implemented in a single use system with the possibility of liquid-contact (wetted) parts being disposed after use. It is a further important aim to provide a pump wherein the moving parts do not directly contact the liquid moving around the system, thus minimising the risk of contamination of the cell culture during use. The invention further seeks to provide a simple design which is easily scalable such that it may be employed with smaller bioreactors, typical of process development systems. Advantageously, the system may be configured for use in both ATF and TFF modes with little adaption of the pump or system required.

According to a first aspect of the invention, there is provided a liquid filtration system comprising: a syringe pump comprising a gas chamber and a movable plunger, wherein the gas chamber has an aperture at a first end and the plunger forms a seal within the internal walls of the chamber; a liquid chamber having two openings, the openings positioned at opposite ends of the chamber and the first opening connected to the aperture of the gas chamber; a bioreactor in fluidic communication with the second opening of the liquid chamber; a filter arranged to filter liquid passing between the bioreactor and the liquid chamber, the filter comprising a permeate outlet for removing filtered liquid; wherein, in use, the plunger may be moved in a reciprocating motion causing a corresponding movement of gas which drives liquid alternately between the liquid chamber and the bioreactor such that liquid passes through the filter and filtered liquid may be removed via the permeate outlet.

With the liquid filtration system according to the present invention, firstly the syringe pump utilised has a simple design which may be scaled to a size appropriate for application in small process development bioreactor systems. The reduced complexity further reduces the possibility of the pump malfunctioning leading to downtime between runs.

A further important aspect is that there is no direct contact between the moving parts of the pump and the liquid to be filtered; rather the driving force of the pump is transferred to the liquid via the movement of air between a gas chamber and liquid chamber. Unlike prior art systems, there is no moving part, such as a diaphragm, in direct contact with the liquid. The latter feature means that the moving parts of the pump do not need to be sterilised or replaced between uses and further, the parts of the system in contact with the liquid, such as the liquid chamber, may be provided as part of a single use product which is disposed of after use. Since there is no contact between the pump and cell culture there is no risk of contamination of the pump from the culture and the culture from the non-sterile air on the pump side.

Another important advantage of this pump arrangement is that it avoids the mechanical stresses on cells inherent in other pumps for example peristaltic, diaphragm or impeller pumps. The arrangement of the present invention does not require any check valves, the correct motion of the liquid being driven by the pump and appropriate connections. This reduces the stress applied to the cells as check valves apply significant forces to the constituents of the liquid as they pass through.

The liquid filtration system according to the present invention may also be applied in both TFF and ATF processes with little or no modification such that it is suitable to be used for a filtration process incorporating phases of both TFF and ATF. The function of the syringe pump arrangement of the present invention approaches that of a positive displacement pump. The system therefore provides an effective pumping action whereby if the plunger is moved by 15 ml the corresponding culture flow is effectively 15 ml.

In certain preferable examples of the present invention, the syringe pump is a through-rod piston pump wherein the plunger is mounted on a rod that moves axially through the chamber.

BRIEF DESCRIPTION OF THE DRAWINGS

Embodiments of the invention will now be described, by way of example only, with reference to the accompanying drawings, in which.

DETAILED DESCRIPTION OF EMBODIMENTS OF THE INVENTION

In the description that follows and in the figures, certain examples of the invention are described. However, it will be appreciated that the invention is not limited to the examples that are described and that some examples may not include all of the features that are described below. It will be evident, however, that various modifications and changes may be made herein without departing from the broader spirit and scope of the invention as set forth in the appended claims.

Figure 1:
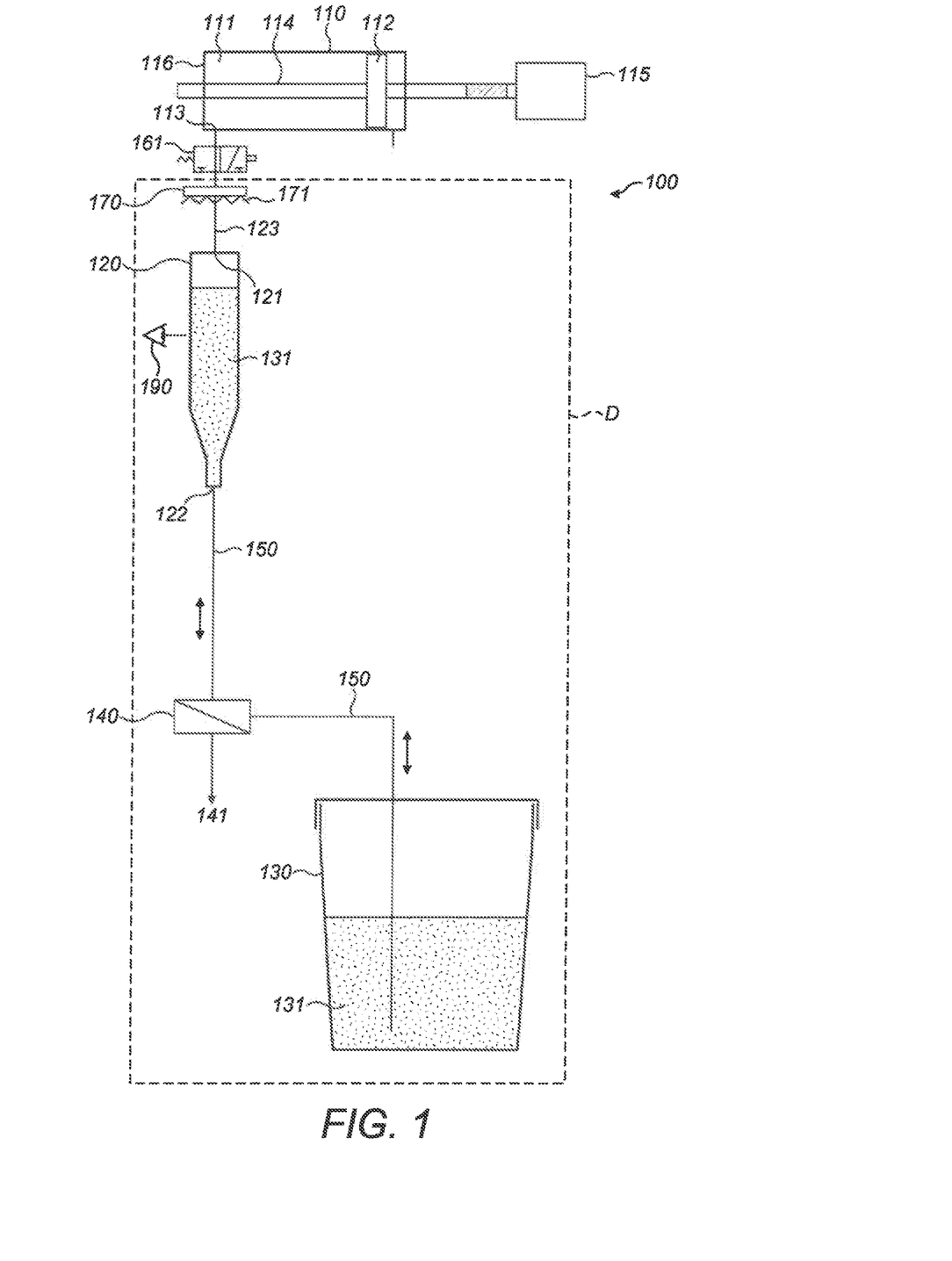
FIG. 1 schematically illustrates a first example of a liquid filtration system according to the present invention.

FIG. 1 schematically illustrates an exemplary liquid filtration system 100 according to the invention. The liquid filtration system 100 includes a syringe pump 110, a liquid chamber 120, a bioreactor 130 and a filter 140. In the example of FIG. 1 each of these components are fluidically connected in series via a liquid line 150, through which a liquid 131, such as a cell culture liquid, can pass. In normal use, the cell culture liquid 131 is stored within the bioreactor 130 and is transported between the bioreactor 130 and liquid chamber 120, via the filter 140 under the action of the syringe pump 110.

The syringe pump 110 comprises a gas chamber 111 and a moveable plunger 112. The plunger 112 is moveable within the gas chamber 111 and fits closely with the internal walls of the gas chamber housing so as to form a substantially air tight seal. In the example of FIG. 1, the gas chamber 111 has one aperture 113, positioned at a first end of the gas chamber 111. The gas chamber 111 may have an elongate, tubular shape such as a cylinder with the plunger 112 moveable through the chamber 111 along the elongate axis and maintaining a seal radially across the cross section of the chamber 111. Using this arrangement, movement of the plunger 112 through the chamber 111 towards the aperture 113 causes a gas, held within the chamber 111, to be expelled through the aperture 113.

In the exemplary arrangement of FIG. 1, the liquid chamber 120 has an elongate, tubular shape with a first 121 and second 122 opening at opposing ends along the elongate axis. As illustrated in FIG. 1, the aperture 113 at the first end of the gas chamber 111 is connected to a first opening 121 of the liquid chamber 120 by a gas connection 123. The second opening 122 of the liquid chamber 120 is in fluidic communication with the bioreactor 130 via the liquid line 150. In normal use, the liquid chamber 120 is at least partially filled with the liquid cell culture solution 131 which similarly fills the liquid line 150 continuously to the bioreactor 130.

The liquid filter 140 is positioned on the liquid line 150 between the bioreactor 130 and liquid chamber 120 such that liquid passing therethrough is at least partially filtered, with the retentate remaining in the system and the filtered permeate exiting the system via the permeate outlet 141. The permeate may be drawn off through the permeate outlet 141 by an external pump (not pictured here). The liquid filter 140 may take a number of different forms and may preferably be a tangential flow filter wherein the flow of liquid is substantially tangential to the filter surface with the permeate passing through to be extracted via the permeate outlet 141. The filter may, for example, be a hollow fibre filter. A pressure difference may be applied across the filter to increase the passage of permeate through the filter 140.

The operation of the syringe pump 110 will now be described in more detail with reference to FIGS. 2A to 2C. As described above, the plunger 112 forms a seal with the internal walls of the housing 116 of the gas chamber 111 to define an internal sealed volume of the gas chamber 111 which holds a gas, such as air, during normal operation. The arrangement of FIG. 2 differs slightly from that of FIG. 1 in that the aperture 113 is disposed on an end of the housing 116 opposing the chamber facing side of the plunger along the elongate axis of the chamber 111. This has little functional bearing on the operation of the pump in comparison to the arrangement of FIG. 1 in which the aperture 113 is disposed on a side wall of the chamber close to a first end which is sealed. It will be appreciated that the aperture can be placed anywhere on the chamber housing 116 with the limitation that its proximity to an end of the chamber will maximise the volume of air within the chamber 111 that may be expelled, the arrangement of FIG. 2 thereby providing an optimal configuration.

Figure 2A:
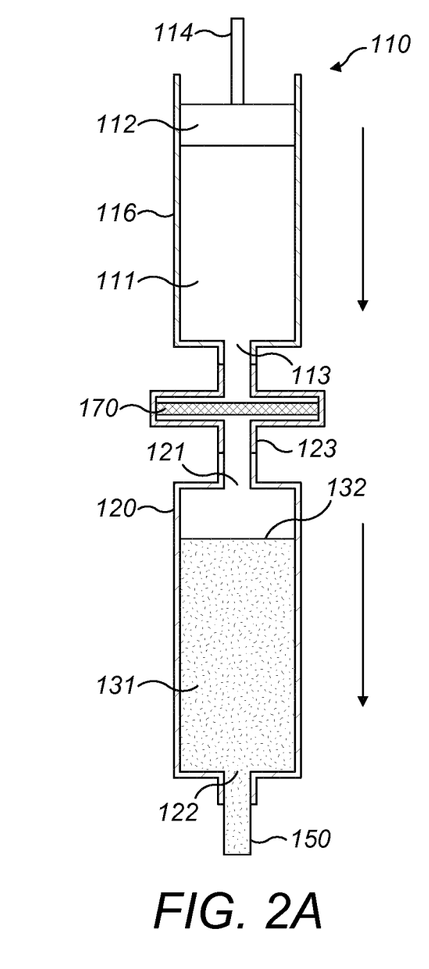
FIG. 2 schematically illustrates the operating of the pump according to the present invention.

FIG. 2A shows a configuration of the pump in which the plunger is fully retracted away from the aperture 113, thereby providing a maximum volume of air within the chamber. As the plunger is moved towards the aperture 113, air within the chamber 111 is compressed and forced out of the aperture 113 through the gas connection 123 into the first opening 121 of the liquid chamber 120. The force of the air entering the liquid chamber 120 provides a pressure, acting on the top surface of the liquid 131 within the chamber. The increasing pressure acts to expel at least a portion of the liquid 132 through the second opening 122 of the liquid chamber 120 into the liquid line 150, as shown in FIG. 2A.

Figure 2B:
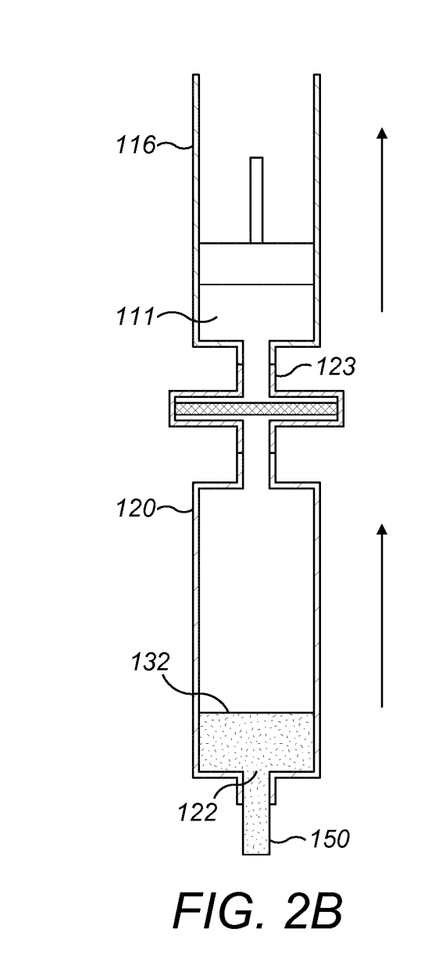
Figure 2C:
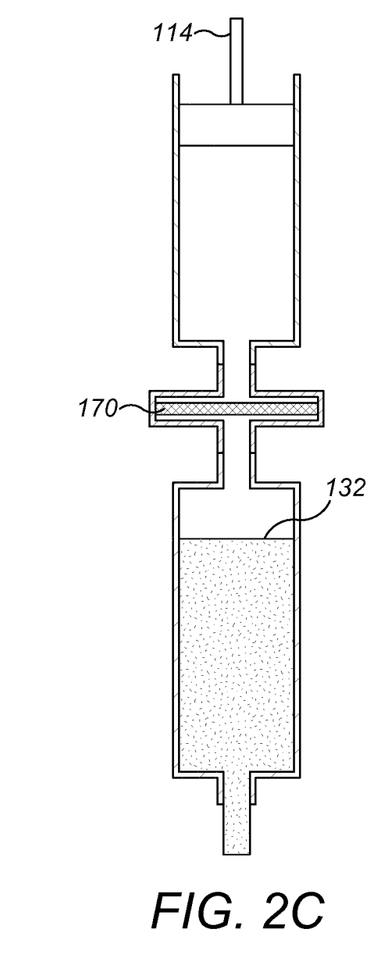

The opposite action of the pump is illustrated by a comparison of FIGS. 2B and 2C, the former showing the pump when the plunger is substantially extended such that the liquid level in the liquid chamber 120 is substantially reduced. As the plunger is retracted in a direction illustrated by the arrows in FIG. 2B, the pressure in the internal volume—as defined by the gas chamber 111, gas connection 123 and portion of the liquid chamber 120 above the liquid level 132—is substantially reduced. This causes liquid to be drawn from the liquid line 150 through the second opening 122 in the liquid chamber 120, filling the liquid chamber 120 such that, when the plunger 112 is fully withdraw, the liquid level returns substantially to the initial level, as shown in FIG. 2C. In this way, a reciprocal motion of the plunger towards and then away from the aperture 113 at the first end of the gas chamber causes liquid 131 in the liquid chamber to be alternately expelled from and drawn in to the liquid chamber 120.

As clear from FIGS. 1 and 2, the plunger 112 of the syringe pump 110 may be mounted on a piston rod 114, which may be aligned axially with and configured to move though the chamber 111. The plunger 112 may be provided on the end of the rod 114, as in the case of FIG. 2, or the piston rod 114 may be a "through rod", as shown in FIG. 1, where it runs axially through the length of the gas chamber 111. The latter arrangement has particular advantages in further exemplary embodiments of the invention, as will be described. The piston rod 114 may be driven by a motor 115 which is configured to provide the necessary alternating motion of the plunger 112 in the pump cycle. The motor may be a servo- or stepper-motor in combination with a lead-screw arrangement to provide precisely controllable speed, acceleration and displacement of the reciprocating motion.

Returning to FIG. 1, it can be seen that, since the liquid 131 fills the liquid line 150 from the bioreactor 130 to the liquid chamber 120, the above-described action of the pump causes liquid from the bioreactor 130 to be drawn through the filter 140 into the liquid chamber 120 and then returned through the filter 140 into the bioreactor 130. The exemplary embodiment of FIG. 1 is therefore suitable to perform alternating tangential flow filtration (ATF) wherein each time liquid 131 passes over the filter 140 a certain amount of permeate is removed via the permeate outlet 141. It will be appreciated that with certain minor additions and modifications, the arrangement of FIG. 1 may be configured to also provide tangential flow filtration in which the liquid circulates in a single direction. In particular, a second liquid line may be added (not shown) to the arrangement of FIG. 1 which is connected directly between the liquid chamber 120 and bioreactor 130, acting as a liquid return line which returns liquid directly from the liquid chamber to the bioreactor, bypassing the filter 140. The liquid line 150 shown in FIG. 1 may therefore act solely as a liquid uptake or liquid inlet line, transporting liquid from the bioreactor through the filter to the liquid chamber. Additionally one or more valves may be added to selectively close the first liquid line 150 and liquid return line. Liquid may then circulate around the system by configuring the valves such that the liquid uptake line is open and the liquid return line is closed while the plunger 112 is moved away from the aperture 113, allowing liquid to be drawn from the bioreactor 130 through the filter 140 into the liquid chamber 120. The valves may be further configured such that the liquid uptake line is closed and the liquid return line is open when the plunger is moved towards the aperture 113, such that liquid within the liquid chamber is expelled and travels through the liquid return line to the bioreactor. In this way, the reciprocating motion of the plunger and synchronous operation of the valves causes the liquid to circulate around a fluidic loop provided by the liquid uptake line and liquid return line. It will be appreciated that, if such a circulating TFF arrangement is used, the filter 140 could equally be placed on the liquid return line.

As important aspect of the liquid filtration system according to the invention, as clear from the above description of FIGS. 1 and 2, is that the transfer of the force from the piston 112 to the liquid 131 is via an intermediary volume of gas confined in the system between the piston-facing surface 132 of the liquid 131 and the plunger. One important beneficial effect of the avoidance of direct contact between the pump and liquid is that the possibility of contamination is significantly reduced. In particular, the arrangement prevents substances deriving from the pump components entering the liquid and therefore negates any associated detrimental effects on the cell culture. Similarly it prevents any remnants from the cell culture contaminating the pump, removing the need for the pump components to be cleaned between runs and therefore reducing the downtime. Another important advantage of this pump arrangement is that it avoids the mechanical stresses on cells inherent in other pumps for example peristaltic, diaphragm or impeller pumps. Furthermore it allows for many of the system components to be provided in a single use package which may be disposed after each run and replaced with a new package, allowing for an increased throughput. In particular, FIG. 1 illustrates how all of the components within box D may be provided as a disposable unit in aseptic form which may be replaced after use with a new package which may simply be connected to the pump 110 via gas line 123. The gas chamber 120 and plunger 112 may form part of fixed system hardware which is reused.

There are a number of additional features which may be implemented in the system 100 to improve operative performance and further increase suitability for application in a single-use aseptic package D. Firstly, a sterile filter 170 may be provided across the gas line 123 between the gas chamber 111 and pump 110, the filter 170 providing a sterile barrier. This further ensures that no substances deriving from the liquid cell culture medium, such as expelled gasses, may reach the components of the pump 110. Similarly it prevents any contamination of the liquid 131 from substances derived from the pump 110 or from outside the system 100. The filter 170 and liquid chamber 120 may be assembled as part of the single use perfusion circuit. A heater 171 may further be arranged adjacent to the filter such that heat may be applied to keep the filter warm and prevent blockage via condensation.

A further feature which may be included to optimise performance of the filtration system 100 is a valve 161 on the gas connection 123 which is configured to seal selectively the gas chamber 111 from the remainder of the system 100. The valve 161 therefore allows for the pump to be sealed when the components of the disposable unit D are replaced between runs.

The valve 161 further allows for the system to be sealed in order to reposition the plunger 121. For optimal operation, in which the maximum amount of liquid is drawn through the filter during each cycle, the high point of liquid 131 within the liquid chamber 120 must be maintained optimally. In particular, when the plunger 112 is fully withdrawn, as illustrated in FIG. 2A, the liquid level 132 within the chamber is preferably near the top end of the chamber near the first opening 121, to which the gas chamber 111 is connected but without contacting the filter 170. This ensures that liquid 131 is moving through the filter 140 during the entirety of the plunger 112 movement range. In the eventuality that the liquid level drops, for example due to outgassing of the cell culture such that the volume of gas between the plunger and liquid level increases, the valve allows for the liquid level to be returned to its optimal height. In particular the gas connection valve 161 may be sealed while the plunger 112 is moved to a position such that, when it is reconnected to the system, the liquid level may be drawn to the optimum height. Similarly the valve 161 may be used to adjust the liquid level on initial priming of the system 100. The valve 161 may take many different forms for example a 3-port 2-way solenoid valve (3/2 valve) may be employed.

In any of the exemplary arrangements of the invention, liquid level control may be achieved by sensing the liquid level in the chamber 120 with a sensor 190. This may be achieved by many different means for example by capacitive means, optically, thermally or ultrasonically.

An alternative (not illustrated in the Figures) to liquid level detection is to adjust the liquid height by drawing liquid up into the liquid chamber 120 via movement of the plunger 112 until it contacts the sterile filter 170 and continuing to move the plunger 112 back. To prevent the sterile filter membrane rupturing once the liquid has made contact with the membrane, air can be introduced passively into the system by a check valve (not pictured) in the air connection 123 with a small cracking pressure rating. At the end of this procedure, the liquid level is known (that is, it is in contact with the membrane) and the plunger 112 can be repositioned and the appropriate liquid level high point determined. This procedure can be repeated regularly as required (as determined through experience with a particular cell culture), or on demand.

Figure 3A:
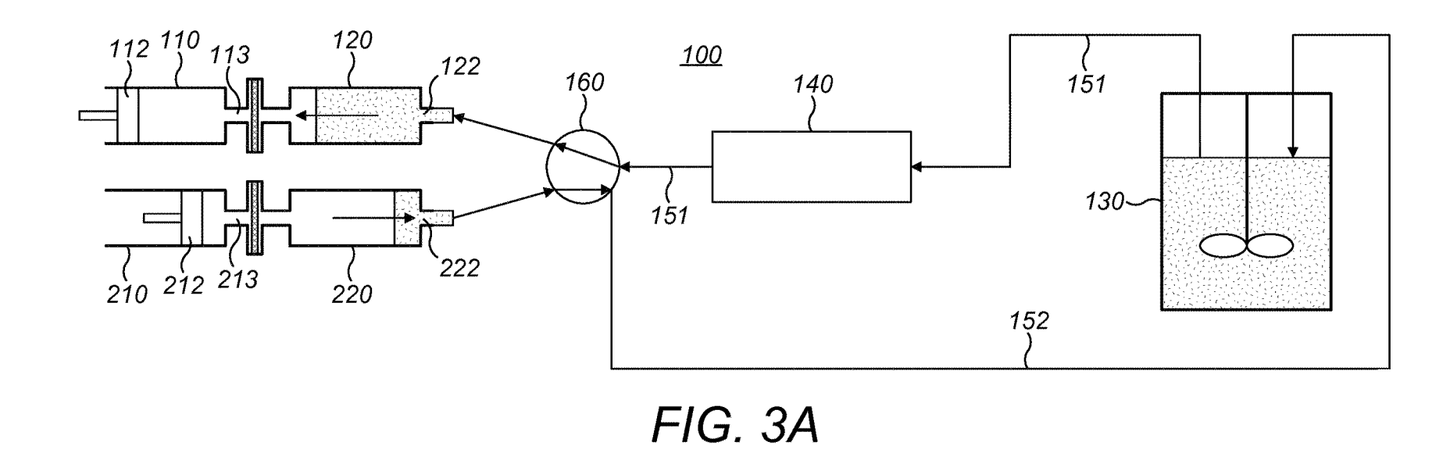
FIG. 3 schematically illustrates an example of the liquid filtration according to the present invention which incorporates two syringe pumps.
Figure 3B:
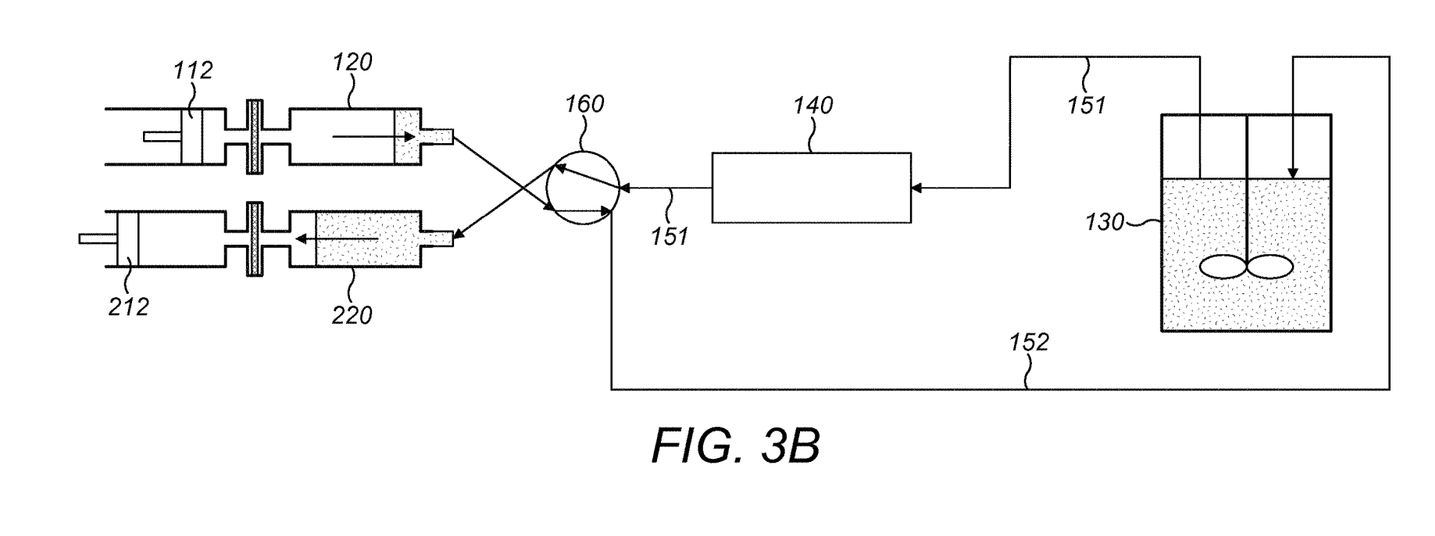

FIGS. 3A and 3B schematically illustrate another exemplary filtration system 100 according to the present invention. The arrangement of FIG. 3 incorporates a second syringe pump 210 connected to a second liquid chamber 220 in the same manner as the arrangement of FIG. 1 or 2. The arrangement of FIG. 3 therefore provides a dual pump arrangement wherein the second openings 122, 222 of both liquid chambers 122, 222 are connected via liquid lines 151, 152, to the filter 140 and bioreactor 130. In particular, under the action of each syringe pump 110, 210, liquid from the bioreactor may be moved through the liquid uptake line 151, through the filter 140, into the liquid chamber 120, 220 of the corresponding pump. Similarly the opening 122, 222 of each liquid chamber 120, 220 is connected via the liquid return line 152 to the bioreactor 130 such that liquid may be returned to the bioreactor 130 upon expulsion from the chamber 120, 220. Although the filter 140 is shown positioned on the liquid uptake line 151, it could equally be placed on the liquid return line 152. The action of the syringe pumps 110, 210 may be coordinated so as to provide ATF in which the respective plungers are synchronised or TFF in which the motion of the plungers is reciprocal, as will be explained.

In order to coordinate the reciprocal action of the dual syringe pumps, a system of one or more valves 160 is used to open and close the respective liquid connections, as illustrated schematically in FIGS. 3A and 3B. The pumps and motor (not pictured) may be configured such that the pump cycles of the plungers are substantially in anti-phase, that is, the plunger 112 of the first pump is retracted while the plunger 212 of the second pump is extended towards the gas aperture 213, as shown in FIG. 3A. The system of one or more valves 160 is configured such that when a plunger is extended such that liquid from that chamber is being expelled, the connection from the liquid chamber to the return line 151 is open and a connection to the uptake line is closed.

At the point in the cycle illustrated by FIG. 3A, the valve system 160 connects the uptake line 151 to the first liquid chamber 120 and the return line 152 to the second liquid chamber 220. Then as the second plunger 212 is withdrawn and the first plunger 112 is extended, as shown in FIG. 3B, the valve system 160 opens the connection of the first liquid chamber 120 to the liquid return line 152 (closing the connection to the uptake line 151) and opens the connection of the second liquid chamber 220 to the liquid uptake line 151 (closing the connection to the return line 151). It will be appreciated that the valve system 160 can be realised in a number of different ways. For example each chamber opening may be connected with two liquid lines, one of the lines of each chamber connected to the main liquid uptake line 151 and the remaining line of each chamber connected to the main liquid return line 152. Each of the four liquid lines leaving the liquid chambers may then be fitted with a pinch valve, the pinch valves configured to provide the necessary coordinated opening and closing of the connections according to the stage of the pump cycle.

Pinch valves provide more gentle handling of cells compared to other valve types such as check valves. The arrangements of the present invention are such that the flow may be managed purely by the control of pinch valves which reduces the stresses exerted on the cells associated with the use of check valves.

Although FIGS. 3A and 3B illustrate the liquid filtration system configured to provide a tangential flow filtration process in which the liquid from the bioreactor circulates around the loop provided by the uptake line 151 and return line 152, an alternating tangential flow process may equally be provided. For example the pump cycles of the pumps could be altered such that they are in phase and the valve system could be configured to close the liquid line which does not include the filter 140 and therefore solely move liquid thought the filter to the bioreactor along one liquid line such that the flow direction through the filter 140 alternates. Furthermore these straightforward configuration changes could be performed during a cell culture run such that combinations of periods of TFF and ATF may be used. The operation of the one or more motors controlling the pumps and the operation of the valve system 160 may be controlled by an external control unit (not shown) such that phases of ATF and TFF may be run in an uninterrupted process by sequencing the valves. Dual purpose labware which can be used in both ATF and TFF modes may be used to control the system.

Figure 4:
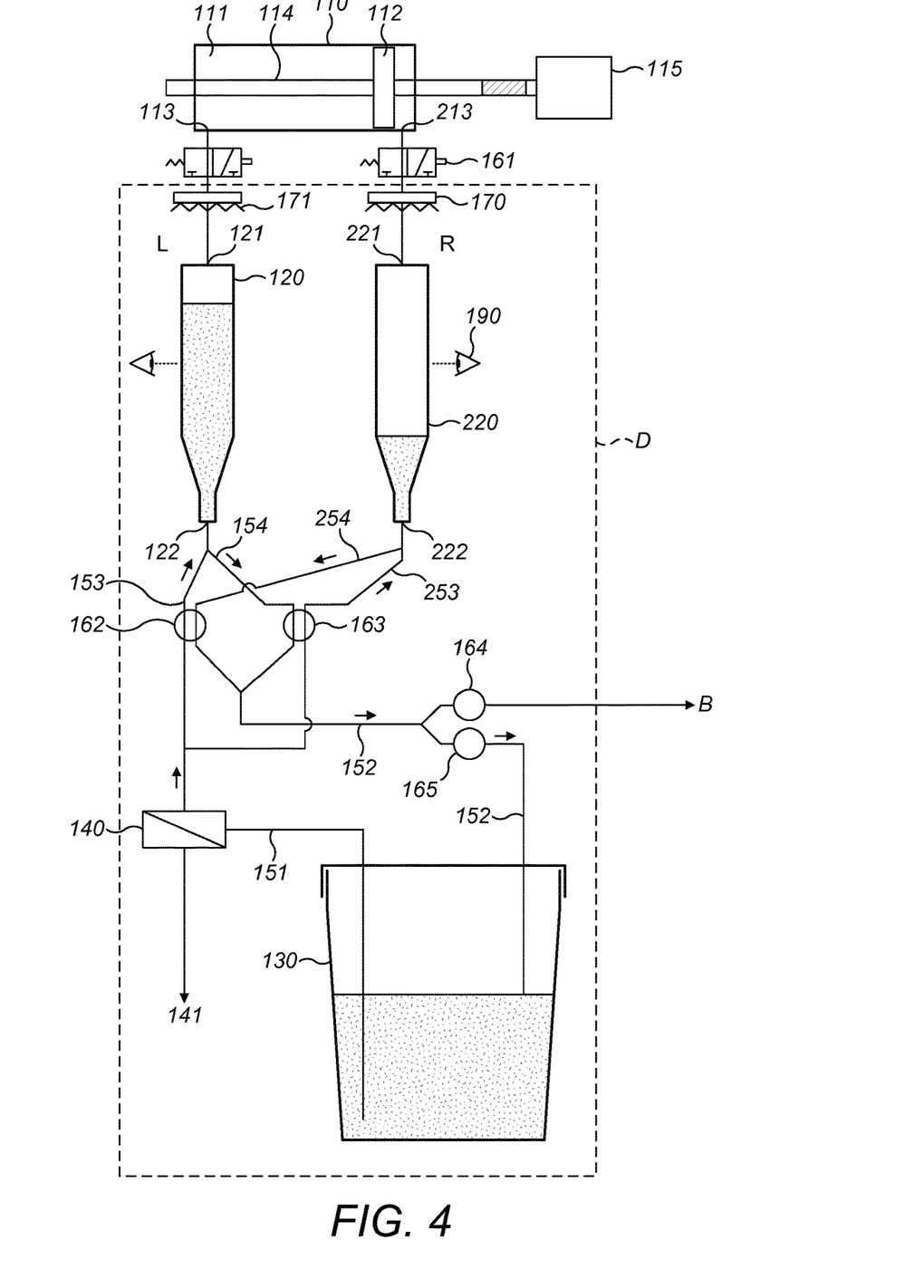
FIG. 4 schematically illustrates an example of the liquid filtration system according to the present invention which incorporates a single syringe pump connected to two liquid chambers.

FIG. 4 is a schematic illustration of a further example of a liquid filtration system according to the present invention. In this arrangement a single syringe pump 110 is used but the gas chamber 111 has two apertures 113, 213 each positioned at opposing ends of the chamber 111. The piston rod 114 is a "through rod" running axially through the chamber 111, wherein the plunger 112 is placed on a middle portion of the rod 114 such that it moves alternately through the chamber 111 between the opposing first and second ends. Since the first 113 and second 213 apertures are positioned near the opposing ends of the chamber 111, gas is expelled through one aperture whilst being drawn into the other aperture. The first and second apertures may be connected to a first 120 and second 220 liquid chamber respectively, each connected in a manner similar to that described with reference to FIGS. 1 to 3. The motion of the plunger 112 therefore causes liquid held in one liquid chamber 120, 220 to be expelled through the opening 122, 222 whilst liquid is drawn through the opening of the other liquid chamber, into the chamber 220, 120.

This simple configuration enables a single reciprocating driving force to simultaneously drive air out of one end of the pump chamber while sucking air in the other end.

FIG. 4 further illustrates how liquid chambers 120, 220 may be connected to the filter 140 and bioreactor 130 to provide continuous perfusion in a TFF arrangement. There is a junction in the liquid line leaving the opening 122, 222 of each chamber such that each splits into two lines, an inlet line 153, 253 connected to the main liquid uptake line 151 and an outlet line 154, 254 connected to the main liquid return line 152. The flow of liquid between the liquid chambers and the remainder of the system is controlled by opening and closing the inlet lines 153, 253 and outlet lines 154, 254 using the valve system 160. In this example the valve system is provided by a number of pinch valves. As the plunger 112 moves to the right of the chamber 111, the first pinch valve 162 is open and the second pinch valve 163 is closed. Liquid is then drawn from the bioreactor through the uptake line 151 via the filter 140 and into the first liquid chamber through the inlet 153. Simultaneously liquid is expelled though the outlet 254 of the second liquid chamber which connects to the liquid return line 152, returning the liquid to the bioreactor 130. The first pinch valve 162 is then closed and the second pinch valve 163 is opened while the plunger 112 moves to the left towards the first end of the chamber 111. Accordingly liquid is drawn from the bioreactor 130, through the filter 140 and into the second liquid chamber 220 via the inlet line 253. Simultaneously liquid is expelled through the outlet line 154 of the first liquid chamber 120 and returned to the bioreactor via the return line 152. By synchronising the operation of pinch valves 162 and 163 with the motion of the syringe pump 110, effectively pulse-free continuous TFF can be achieved. As with all examples of the invention, the switching time of the valves may be sufficiently short that there is no significant effect on the operation of continuous flow TFF-based perfusion.

As described above, the operation of the one or more motors controlling the pumps and the operation of the valve system 160 may be controlled by an external control unit (not shown) such that phases of ATF and TFF may be run in an uninterrupted process by sequencing the valves 162, 163. Dual purpose labware which can be used in both ATF and TFF modes may be used to control the system.

Several other features may be introduced to the above described examples of the invention to provide further functionality.

Once the desired cell density has been achieved in the bioreactor vessel 130, the user may wish to prevent it rising higher, or to reduce the cell density by bleeding cell culture out of the system periodically. In prior art devices, this function requires separate pumps for cell bleeding and perfusion. However, with the filtration system according to the present invention, it can simply be provided by a bleed outlet B disposed on the return line 152, as illustrated in FIG. 4. The bleed outlet B may be provided by a valved junction in the return line, one branch of which returns to the bioreactor 130, the other directs fluid out of the system through the bleed outlet B. The branches in the return line 152 may be provided with pinch valves 164, 165 which can open and close the lines to control the bleed function. During normal operation, a bleed line pinch valve 164 is closed and a return line pinch valve 165 is open. When bleeding cells, the bleed line pinch valve 164 opened and return line pinch valve 165 is closed such that the action of the syringe pump pushes liquid out of the liquid chamber and through the bleed outlet B, rather than being returned to the bioreactor vessel 130.

In a further alternative within the scope of the invention the fluid cavity may be continuous with the head space of the bioreactor, the path including a control valve (not shown) to allow an increase and decrease in pressure in the liquid chamber as required. The continuous path allows equilibrium of the gas composition in the headspace with that of the bioreactor 130 to avoid any negative impact on the cells.

In addition to a liquid level sensor, other sensors may be incorporated into the system, the sensors configured to measure, for example, pressure, cell density and cell viability. Data from the sensors may be received by the control unit and the control unit may control various aspects of the system, such as the valve system, pump plungers, the motor or bleed function, in response to the sensed data.

With the liquid filtration system according to the present invention, firstly the syringe pump utilised has a simple design which may be scaled to a size appropriate for application in small process development bioreactor systems.

The reduced complexity further reduces the possibility of the pump malfunctioning leading to downtime between runs and also reduces the cost of manufacture such that it may implemented as a single use device. A further important aspect is that there is no direct contact between the moving parts of the pump and the liquid to be filtered; rather the driving force of the pump is transferred to the liquid via the movement of air between a gas chamber and liquid chamber. The latter feature means that the moving parts of the pump do not need to be sterilised or replaced between uses and further, the parts of the system in contact with the liquid, such as the liquid chamber, may be provided as part of a single use product which is disposed of after use. The liquid filtration system according to the present invention may also be applied in both TFF and ATF processes with little or no modification such that it is suitable to be used for a filtration process incorporating phases of both TFF and ATF in a single system.

The invention claimed is:

1. A liquid filtration system comprising:
   a syringe pump comprising a gas chamber and a movable plunger, wherein the gas chamber has a first aperture at a first end and the plunger forms a seal within the internal walls of the chamber;
   a liquid chamber having two openings, the openings positioned at opposite ends of the chamber and the first opening connected to the first aperture of the gas chamber;
   a bioreactor in fluidic communication with the second opening of the liquid chamber; and
   a filter arranged to filter liquid passing between the bioreactor and the liquid chamber, the filter comprising a permeate outlet for removing filtered liquid;
   wherein the plunger is movable in a reciprocating motion causing a corresponding movement of gas which drives liquid alternately between the liquid chamber and the bioreactor such that liquid passes through the filter and filtered liquid may be removed via the permeate outlet; and
   wherein there is no direct contact between the movable plunger of the syringe pump and the liquid to be filtered.

2. The liquid filtration system of claim 1 wherein the syringe pump is a first syringe pump and the liquid chamber is a first liquid chamber, and further comprising:
   a second syringe pump; and
   a second liquid chamber having two openings, the openings positioned at opposing ends of the second liquid chamber, wherein:
      the first opening of the second liquid chamber is connected to an aperture of the second syringe pump; and
      the second opening of the second liquid chamber is in fluidic communication with the bioreactor and filter;
   wherein the first and second syringe pumps act cooperatively to drive the liquid in the system.

3. The liquid filtration system of claim 2 further comprising:
   a liquid uptake line providing the fluidic communication from the bioreactor to the first and second liquid chambers;
   a liquid return line providing the fluidic communication from the first and second liquid chambers to the bioreactor, the filter positioned on either the liquid uptake line or return line; and
   a valve system comprising one or more valves, the valve system configured to direct liquid expelled from the first liquid chamber or the second liquid chamber into the return line and ensure liquid is drawn into the first liquid chamber or the second liquid chamber from the uptake line.

4. The liquid filtration system of claim 3 wherein the valve system comprises one or more pinch valves configured to:
   close a connection from a liquid chamber of the first and second liquid chambers to the uptake line and open a connection to the return line when liquid is leaving the liquid chamber; and
   open the connection from the liquid chamber to the uptake line and close the connection to the return line when liquid is entering the liquid chamber.

5. The liquid filtration system of claim 2 further comprising:
   a first sterile filter positioned between the aperture of the gas chamber of the first syringe pump and the first opening of the first liquid chamber, and a second sterile filter positioned between the aperture of the gas chamber of the second syringe pump and the first opening of the second liquid chamber, the first and second sterile filters configured to permit the passage of gas while maintaining sterility within a liquid path of the liquid filtration system.

6. The liquid filtration system of claim 5 further comprising:
   one or more heater elements configured to heat the first and second sterile filters.

7. The liquid filtration system of claim 1 wherein the liquid chamber is a first liquid chamber, and further comprising:
   a second aperture in the gas chamber, the second aperture positioned at the opposite end of the gas chamber to the first aperture and separated from the first aperture by the plunger;
   a second liquid chamber having two openings at opposing ends of the chamber, the first opening connected to the second aperture of the gas chamber and the second opening in fluidic communication with the bioreactor and filter;
   a liquid uptake line providing the fluidic communication from the bioreactor to the first and second liquid chambers;
   a liquid return line providing the fluidic communication from the first and second liquid chambers to the bioreactor, the filter positioned on either the liquid uptake line or return line; and
   a valve system comprising one or more valves, the valve system configured to direct liquid expelled from a chamber of the first and second liquid chambers into the return line and ensure liquid is drawn into a chamber of the first and second liquid chambers from the uptake line;
   wherein, in use, movement of the plunger through the gas chamber causes liquid to be expelled from one liquid chamber of the first and second liquid chambers into the return line whilst liquid is drawn in to the other liquid chamber of the first and second liquid chambers from the uptake line, the reciprocal movement of the plunger thereby providing a substantially continuous flow of liquid within the system.

8. The liquid filtration system of claim 7 further comprising:
a first sterile filter positioned between the first aperture of the gas chamber of the syringe pump and the first opening of the first liquid chamber, and a second sterile filter positioned between the second aperture of the gas chamber of the syringe pump and the first opening of the second liquid chamber, the first and second sterile filters configured to permit the passage of gas while maintaining sterility within a liquid path of the liquid filtration system.

9. The liquid filtration system of claim 8 further comprising:
one or more heater elements configured to heat the first and second sterile filters.

10. The liquid filtration system of claim 1 further comprising:
one or more gas connection valves positioned between the gas chamber and liquid chamber, the one or more gas connection valves configured to seal the gas chamber from the remaining system, allowing the plunger to be repositioned whilst maintaining the pressure in the liquid chamber.

11. The liquid filtration system of claim 1 further comprising:
a sterile filter positioned between the aperture of the gas chamber and the first opening of the liquid chamber, the sterile filter configured to permit the passage of gas while maintaining sterility within a liquid path of the liquid filtration system.

12. The liquid filtration system of claim 11 further comprising:
one or more heater elements configured to heat the sterile filter.

13. The liquid filtration system of claim 1 further comprising:
a bleed outlet (B) positioned on a liquid return line providing fluidic communication from the liquid chamber to the bioreactor, the bleed outlet (B) configured to provide means to selectively divert liquid returning to the bioreactor out of the system.

14. The liquid filtration system of claim 1 further comprising
one or more sensors configured to determine one or more parameters of a liquid in the system, wherein the parameters include one or more of:
a liquid level, pressure, cell density, cell viability.

15. The liquid filtration system of claim 1 further comprising:
a motor configured to control to the motion of the plunger of the syringe pump.

16. The liquid filtration system of claim 15 further comprising:
a control unit configured to control one or more of:
the motion of the plunger;
the valve system;
the motor; such that the flow of the liquid within the system may be controlled.

17. The liquid filtration system of claim 1 wherein the liquid chamber has an elongate, tubular shape, and wherein the two openings are positioned at opposite ends along an elongate axis of the liquid chamber.

18. A method for filtering a liquid using a liquid filtration system, the system comprising:
a syringe pump comprising a gas chamber and a movable plunger, wherein the gas chamber has a first aperture at a first end and the plunger forms a seal within the internal walls of the chamber;
a liquid chamber having two openings, the openings positioned at opposite ends of the chamber and the first opening connected to the first aperture of the gas chamber;
a bioreactor in fluidic communication with the second opening of the liquid chamber; and
a filter arranged to filter liquid passing between the bioreactor and the liquid chamber, the filter comprising a permeate outlet for removing filtered liquid;
the method comprising:
moving the plunger reciprocally towards and away from the first aperture at the first end of the gas chamber such that gas is alternately expelled from and drawn into the gas chamber, the movement of gas alternately driving the liquid between the liquid chamber and bioreactor such that liquid passes through the filter; and
removing filtered liquid through the permeate outlet of the filter,
wherein there is no direct contact between the movable plunger of the syringe pump and the liquid to be filtered.

19. The method of claim 18 wherein the syringe pump is a first syringe pump and the liquid chamber is a second liquid chamber, and wherein the liquid filtration system further comprises:
a second syringe pump;
a second liquid chamber having two openings, the openings positioned at opposing ends of the chamber wherein
the first opening is connected to an aperture of the second syringe pump; and
the second opening is in fluidic communication with the bioreactor and filter; the method further comprising:
moving the second plunger cooperatively with the first plunger so as to drive the liquid between both the first and second liquid chambers and the bioreactor.

20. The method of claim 19 wherein the liquid filtration system further comprises:
a liquid uptake line providing the fluidic communication from the bioreactor to the first and second liquid chambers;
a liquid return line providing the fluidic communication from the first and second liquid chambers to the bioreactor, the filter positioned on either the liquid uptake line or return line; and
a valve system comprising one or more valves, the valve system configured to direct liquid expelled from a chamber of the first and second liquid chambers into the return line and ensure liquid is drawn into a chamber of the first and second liquid chambers from the uptake line;
the method further comprising:
connecting a liquid chamber of the first and second liquid chambers to the return line with the valve system when the corresponding plunger is moved towards the aperture; and
connecting a liquid chamber of the first and second liquid chambers to the uptake line with the valve system when the corresponding plunger is moved away from the aperture, such that liquid flows around the system in a continuous direction.

21. The method of claim 18 wherein the liquid chamber is a first liquid chamber, and wherein the liquid filtration system further comprises:

a second aperture in the gas chamber, the second aperture positioned at the opposite end of the gas chamber to the first aperture and separated from the first aperture by the plunger; and a second liquid chamber having two openings at opposing ends of the chamber, the first opening connected to the second aperture of the gas chamber and the second opening in fluidic communication with the bioreactor and filter;

a liquid uptake line providing the fluidic communication from the bioreactor to the first and second liquid chambers;

a liquid return line providing the fluidic communication from the first and second liquid chambers to the bioreactor, the filter positioned on either the liquid uptake line or return line; and a valve system comprising one or more valves, the valve system configured to direct liquid expelled from a chamber of the first and second liquid chambers into the return line and ensure liquid is drawn into a chamber of the first and second liquid chambers from the uptake line;

the method further comprising:

connecting the first liquid chamber to the return line and the second liquid chamber to the uptake line with the valve system when the plunger is moved towards the first aperture; and connecting the first liquid chamber to the uptake line and the second liquid chamber to the return line with the valve system when the plunger is moved towards the second aperture, such that liquid flows around the system in a continuous direction.

* * * * *

UNITED STATES PATENT AND TRADEMARK OFFICE
CERTIFICATE OF CORRECTION

| | |
|---|---|
| PATENT NO. | : 11,473,047 B2 |
| APPLICATION NO. | : 16/311522 |
| DATED | : October 18, 2022 |
| INVENTOR(S) | : Grant |

It is certified that error appears in the above-identified patent and that said Letters Patent is hereby corrected as shown below:

In the Claims

Column 13, Line 51, Claim 15 "to control to the motion" should read --to control the motion--.

Signed and Sealed this
Twenty-eighth Day of February, 2023

Katherine Kelly Vidal
*Director of the United States Patent and Trademark Office*